(12) United States Patent
Kogan

(10) Patent No.: US 6,359,964 B1
(45) Date of Patent: Mar. 19, 2002

(54) X-RAY ANALYSIS APPARATUS INCLUDING A PARABOLIC X-RAY MIRROR AND A CRYSTAL MONOCHROMATOR

(75) Inventor: Vladimir A. Kogan, Almelo (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/447,540

(22) Filed: Nov. 23, 1999

(30) Foreign Application Priority Data

Nov. 25, 1998 (EP) ............................................. 98203982

(51) Int. Cl.⁷ .......................................... G01N 23/201
(52) U.S. Cl. .............................. 378/87; 378/70; 378/84
(58) Field of Search ................................ 378/84, 70, 87

(56) References Cited

U.S. PATENT DOCUMENTS 5,551,587 A * 9/1996 Keppel et al. ................. 216/24
6,081,580 A * 6/2000 Grodzins et al. ............. 378/87
6,094,471 A * 7/2000 Silver et al. ................... 378/84

FOREIGN PATENT DOCUMENTS

JP          406130002 A  *  5/1994  ......... G01N/23/201

OTHER PUBLICATIONS

"Performance of Beamline X8C at the NSLS", Alkire et al, vol. A352, No. 3, Jan. 1, 1995, pp. 535–541.
"X–Ray Optics for Materials Research", Proceedings of the Fifth European Powder Diffraction Conference, May 25–18, 1997, Material's Science Forum, vols. 278–281 (1998), pp. 227–235.

* cited by examiner

*Primary Examiner*—David P. Porta
*Assistant Examiner*—Pamela Hodben

(57) ABSTRACT

An apparatus for X-ray analysis of materials advantageously utilizes a parabolic multilayer mirror for parallelizing the X-rays. Moreover, it may be desirable to monochromatize the parallelized radiation, for example by means of a crystal monochromator. According to the invention an influencing device for the X-rays is constructed as a single mechanical unit comprising a combination of an X-ray mirror (46) and a monochromator (48). This unit (66) can be arranged in the analysis apparatus in at least two positions (74, 76) in such a manner that the X-rays travel via the X-ray mirror (46) and the monochromator (48) in the first position (74) whereas the X-rays travel only via the X-ray mirror (46) in the second position (76). Consequently, no separate units comprising only an X-ray mirror or a combination of an X-ray mirror and a monochromator are required, so that a substantial saving in costs is achieved.

6 Claims, 5 Drawing Sheets

X-RAY ANALYSIS APPARATUS INCLUDING A PARABOLIC X-RAY MIRROR AND A CRYSTAL MONOCHROMATOR

FIELD OF THE INVENTION

The invention relates to an X-ray analysis apparatus which includes:
- a sample location for receiving a sample to be examined,
- an X-ray source for irradiating the sample by means of X-rays,
- a detector for detecting X-rays generated in the sample,
- an influencing device which is constructed as a single mechanical unit, serves to influence the X-rays, and is arranged in a beam path between the X-ray source and the detector,
  - said device including a monochromatizing element and an X-ray mirror with a second-order reflecting surface, at least one of said two X-ray optical elements being situated in said beam path,
- a frame for positioning at least the influencing device in the beam path between the X-ray source and the detector.

DESCRIPTION OF PRIOR ART

An influencing device for influencing the X-rays in an apparatus of this kind is known from "Proceedings of the Fifth European Powder Diffraction Conference", May 25–28, 1997, Materials Science Forum, Vols. 278–281 (1998), pp. 227–235, entitled "X-ray Optics for Materials Research".

The cited article, notably the FIGS. 2 and 3 and the accompanying description, discloses an influencing device which is to be arranged in an X-ray beam originating from a line-shaped X-ray source, such as the focal line of an X-ray tube for diffraction purposes. The influence exerted on the X-ray beam by the known device consists in the parallelization and monochromatization of the beam. To this end, the known device includes a graded multilayer X-ray mirror of parabolic shape which is arranged in the beam path of the X-rays and is succeeded by a germanium monochromator crystal having two reflecting surfaces. Both X-ray optical elements (the mirror and the monochromator) are accommodated in a single housing, so that the known influencing device is constructed as a single mechanical unit.

For X-ray analysis of materials to be examined it is sometimes desirable to irradiate the sample to be examined by means of an X-ray beam with very little divergence. This situation occurs, for example for the analysis of thin layers, for measurement of reflectivity, and for powder diffraction. Analysis of thin layers is a technique frequently used for the examination of materials for integrated electronic circuits. In such case it aims to determine the layer thickness as well as the mass density of the layer by means of a single measurement; furthermore, often it is also desirable to determine crystal defects and the content of a given chemical phase in the relevant layer. During all such measurements the X-ray beam is made to strike the (flat) sample surface at a suitably defined small angle. During measurement of reflection from a thin layer, the X-ray beam is also made to strike the (flat) sample surface at a suitably defined small angle; this small angle of incidence is varied so as to control the penetration depth of the X-rays in the layer and hence render the analysis of the various quantities in the layer dependent on the depth in the layer. Making an X-ray beam strike at such a small angle in a suitably defined manner, requires a high degree of parallelism of the incident X-ray beam. In the case of powder diffraction it may occur that the sample has a rough or a slightly curved surface; irradiation by means of a parallel beam then ensures that the measurements are not dependent on said surface condition. Moreover, in the case of irradiation by means of a parallel beam the measurements are not sensitive to displacements of the sample in the beam.

The above measurements require a divergence which is less than from 0.03° to 0.07°, depending on the application. According to a known method of realizing an extremely parallel X-ray beam, the X-ray beam emanating from a narrow X-ray focus (for example, a line focus having a width of 40 m) is made to be incident on a narrow gap (for example, having a width of 40 $\mu$m) which extends parallel to the line focus. When the distance between the line focus and the gap amounts to, for example 100 mm, a divergence of the X-ray beam of the order of magnitude of 0.025° is thus achieved. Such a small divergence, however, is achieved by intercepting the major part of the X-rays, so at the expense of the radiation intensity, so that measurements take much more time or a much poorer signal-to-noise ratio has to be accepted.

When use is made of an X-ray mirror, the X-ray beam originating from the narrow line focus can be converted into a practically parallel beam, so that the loss of intensity is substantially smaller. This is because in that case all radiation incident on the X-ray mirror from the line focus contributes to the intensity in the outgoing beam. This can be illustrated on the basis of the following numerical example: it is assumed that the line focus emits X-rays in a plane perpendicular to the line focus at an angle of 180° (line focus on a flat anode).

Comparing the combination formed by the line focus and the gap with the combination consisting of the line focus and the X-ray mirror, a further calculation reveals that the first mentioned combination utilizes a fraction of $1.3 \times 10^{-4}$ of the emitted radiation with a divergence of 0.023°. For the latter combination it is assumed that the distance between the mirror and the line focus is 100 mm, so that the line focus is seen at an angle of 0.025° from the mirror, also being the divergence of the X-ray beam reflected by the mirror. In this situation it is readily possible to realize a configuration in which the mirror is seen at an angle of 1° from the line focus. It appears that in this situation a fraction of $1°/180°=5.5 \times 10^{-3}$ of the emitted radiation is used with a divergence of 0.025°. The yield of the mirror is, therefore, approximately 20 times higher, taking into account a reflectivity of 50% of the X-ray mirror.

In X-ray analysis it is sometimes also desirable to irradiate the sample to be examined by means of an X-ray beam which has a very small divergence and has also been monochromatized, meaning that only one of the two lines of an X-ray doublet is used (for example, the spectral lines $K_1$ and $K_2$ of a copper anode), so that the other line must be removed from the beam spectrum. This situation occurs, for example in the case of high-resolution measurements during X-ray diffraction, such as measurements on perfect monocrystals (for example, pure silicon as used in the semiconductor industry) or measurements on nearly perfect structures, such as thin films in the semiconductor industry, or measurements on multilayer structures for X-ray reflection.

The desired monochromatization is realized in a known manner by reflection of the X-ray beam by a crystal monochromator. Such a monochromator can pass radiation only with a divergence of about $3 \times 10^{-3}$°. The gain obtained by using a mirror therefore can be estimated as follows. Using an X-ray mirror a fraction of 1° of the radiation emitted in an angle of 180° can be collected by the mirror, which fraction is indicated as the useful yield of the line focus. A first situation consisting of the combination of the line focus and a crystal monochromator can be compared with a second situation consisting of the combination of the line focus and the mirror followed by the crystal monochromator. In the first situation 0.3% (0.003° of 1°) of the useful yield of the line focus is used. In the second situation the whole useful yield is collected by the mirror. Because an X-ray has a reflection efficiency of about 50% and because of imperfections in the reflecting surface of the mirror, eventually 35% of the radiation collected by the mirror is reflected, having a divergence of 0.025°. Only a part of that reflected fraction having a divergence of 0.003° (so about 12%) is accepted by the monochromator so that eventually about 4.2% (35%×12%) of the useful yield of the line focus will leave the monochromator. By this numerical example it is shown that the yield of the combination mirror-monochromator is about 14 times the yield of monochromator alone.

As has already been described, depending on the application, an X-ray beam having a small divergence or an X-ray beam having a small divergence in combination with a strong monochromatization is desired. The known influencing device as disclosed in the cited article is only suitable to deliver the latter type of X-rays. If an X-ray beam having solely a small divergence were desired, a separate unit comprising only an X-ray mirror would have to be used. For equipment which must be capable of performing both types of measurement, therefore, both these (expensive) elements would have to be purchased.

SUMMARY OF THE INVENTION

It is an object of the invention to provide an X-ray analysis apparatus which is suitable for both types of measurements but in which it is not necessary to have both elements separately available. This object is achieved according to the invention in that:

the influencing device is constructed so as to include a first radiation channel which comprises the X-ray mirror and the monochromatizing element, and a second radiation channel which comprises only the X-ray mirror, the influencing device, constructed as a single mechanical unit, and the frame of the apparatus are both provided with co-operating positioning means which are constructed in such a manner that the influencing device in the apparatus can occupy, at option, a first position in which the first radiation channel is positioned in said beam path, or a second position in which the second radiation channel is positioned in said beam path.

The invention is based on the recognition of the fact that it is possible to construct an X-ray mirror which is wider than necessary for use in combination with the monochromatizing element. By arranging the influencing device in a first position in the apparatus, the mirror can be irradiated in such a manner that the radiation reflected by the X-ray mirror subsequently traverses the monochromatizing element. This constitutes the first radiation channel which thus produces parallel, monochromatized radiation. When the influencing device is arranged in a second position in the apparatus, the mirror can be also irradiated in such a manner that the radiation reflected by the X-ray mirror can be taken up directly, i.e. without traversing the monochromatizing element. This constitutes the second radiation channel which thus yields parallelized radiation only. Consequently, both types of radiation can be made available merely by arranging the influencing device in a different position in the apparatus.

Attractive embodiments of the invention are defined in the dependent Claims.

BRIEF DESCRIPTION OF THE DRAWINGS

The invention will be described in detail hereinafter with reference to the Figures. Therein.

DETAILED DESCRIPTION OF THE PREFERRED EMBODIMENTS

Figure 1:
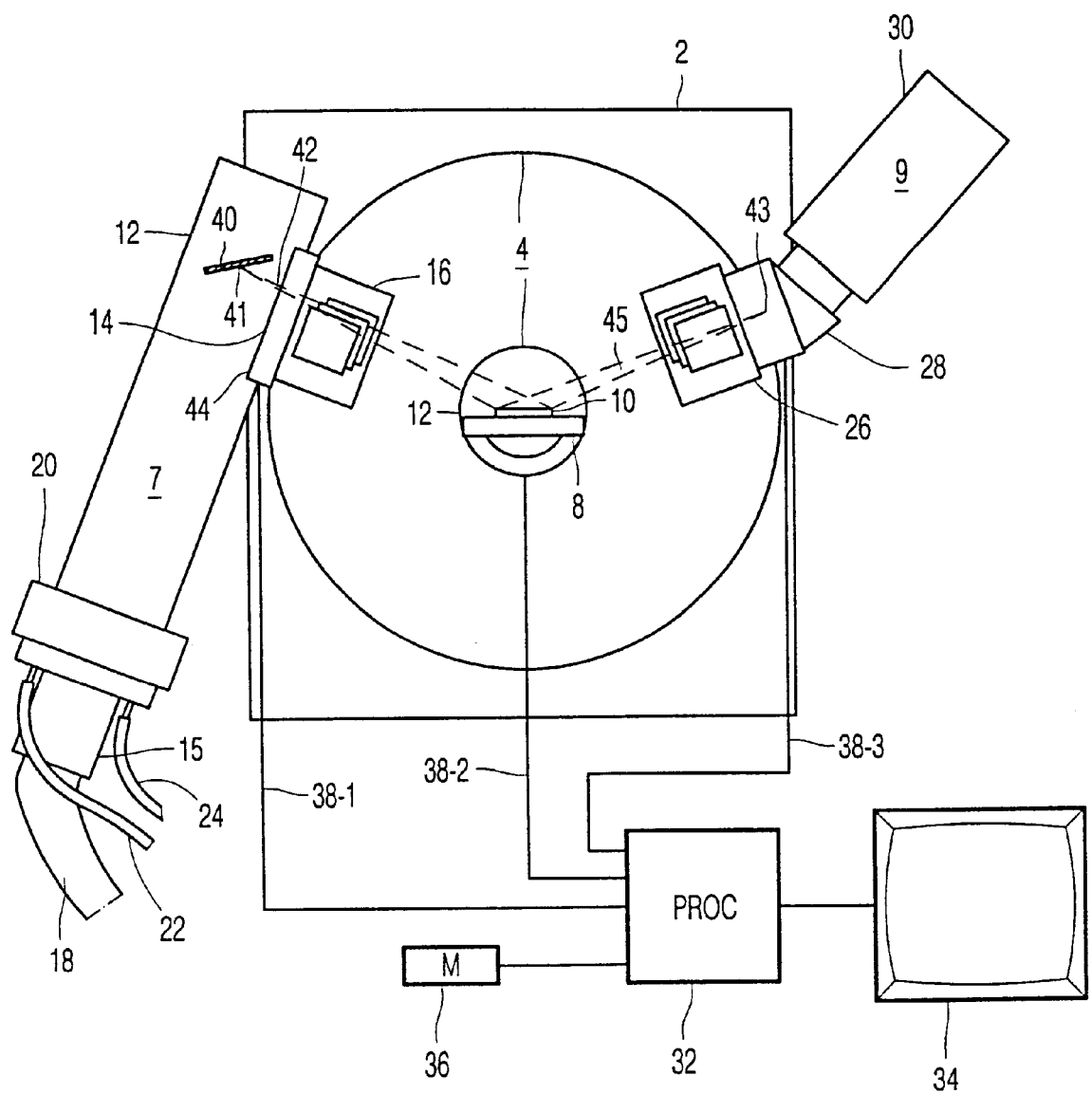
FIG. 1 is a diagrammatic representation of an X-ray analysis apparatus in which the invention can be used.

FIG. 1 is a diagrammatic representation of a known X-ray analysis apparatus, in this case being an X-ray diffraction apparatus. Therein, a goniometer 4 is mounted on a frame 2. The goniometer 4 can be provided with an angular encoder for measuring the angular rotation of the X-ray source 7 which is mounted thereon and of the detector device 9 which is also mounted thereon. The goniometer, moreover, is provided with a sample holder 8 on which a sample 10 is arranged. An angular encoder may be provided on the sample holder for cases where measurement of the angular rotation of the sample is important. The X-ray source 7 includes a holder 12 for an X-ray tube (not shown in the Figure) which is secured in the holder by way of a fixing ring 20. The X-ray tube includes a high-voltage connector 15 for applying the high-voltage and the filament current to the X-ray tube via the high-voltage cable 18. Supply and discharge ducts 22 and 24 for the cooling water of the X-ray tube are provided at the same side of the X-ray tube. The tube holder 12 also includes an exit window for X-rays 44 and a unit 16 for parallelization of the X-ray beam (a Soller slit unit). The plates of the Soller slit unit 16 are parallel to the plane of drawing in such a way that the X-ray beam generated by the X-ray source 7 illuminates the sample 10 with a divergent beam. The detector device 9 consists of a holder 26 for a Soller slit unit, a holder 28 for a monochromator crystal, and a detector 30. The plates of the Soller slit unit in holder 28 are also parallel to the plane of drawing. If the X-ray source and the detector are both rotatable about the sample it is not necessary for the sample to be mounted so as to be rotatable. However, it is alternatively possible to mount the X-ray source so as to be stationary as it may sometimes be necessary in the case of voluminous and heavy X-ray sources. In that case the specimen holder as well as the detector should be rotatable.

The X-ray diffraction apparatus shown in FIG. I also includes a processing device for processing the various measured data. The processing device consists of a central processing unit 32 with a memory unit 36 and a monitor 34 for the presentation of the various data and for the display of the measured and calculated result. The X-ray source 7, the detector device 9 and the specimen holder 8, mounted on the goniometer 4, are all provided with a unit (not shown) for determining the angular position of the relevant element with respect to the scale graduation of the goniometer. A signal representing this angular position is applied, via =connection leads 38-1, 38-2 and 38-3, to the central processing unit 32.

FIG. 1 shows a so-called Bragg-Brentano arrangement, which means that the X-rays emanating from a single point are apparently focused in one point again after reflection by the sample, provided that the surface of the sample is tangent to a circle through the point of origin and the focal point. The sample 10 is irradiated by means of X-rays originating from the X-ray source 7. In the X-ray source there is diagrammatically represented an anode 40 which forms part of the X-ray tube which is not shown in detail in this Figure. In the anode 40 the X-rays are generated in a customary manner by exposing the anode to high-energetic electrons. Thus, in the anode there are generated X-rays 42 which emanate via X-ray window 44. Said point of origin in the arrangement shown in FIG. 1 is not formed by a single point, but by a line focus 41 on the anode which extends perpendicularly to the plane of drawing. Said focal point is formed by the point of union 43 of the beam 45 leaving the sample at the area of the entrance of the detector 30. Therefore, this arrangement has a focusing effect only in the plane of drawing.

As has already been stated, some measurements require a divergence which is less than from 0.03° to 0.07°, depending on the application. This small divergence can be achieved in the arrangement of FIG. 1 by intercepting the major part of the X-rays by means of a small gap (not shown) having a width of, for instance, 40 m , which can be placed after the Soller slit unit 16. A substantial part of the radiation intensity generated by the X-ray tube is then lost. This drawback can be avoided by using the combination of an X-ray mirror and a monochromator or by using an X-ray mirror alone. This means that the said 40 m g ap and the monochromator crystal present in the holder 28 of the detector device 9 of FIG. 1, according to the invention can be omitted and replaced by an influencing device which includes several radiation channels for influencing the X-rays.

Figure 2:
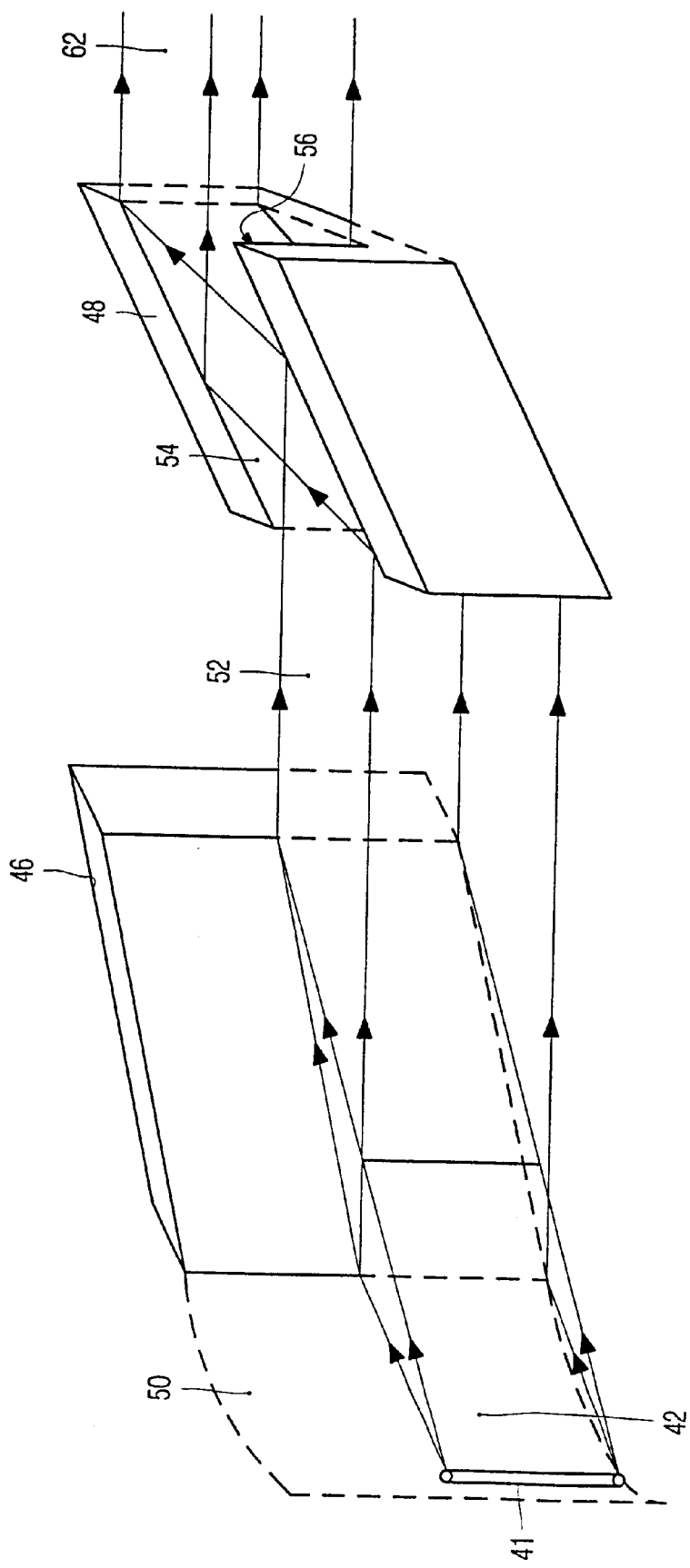
FIG. 2 is a diagrammatic representation of the beam path in an assembly consisting of an X-ray mirror and a monochromatizing element.

FIG. 2 shows diagrammatically the dimensions and relative positions of the X-ray mirror 46 and the monochromatizing element 48 which both form part of the influencing device which can be arranged in the beam path between the X-ray source 7 and the detector 9. The X-rays originate from the line focus 41 on the anode 40 (not shown in FIG. 2), which line focus 41 extends in the focal line of the (partly imaginary) parabolic surface 50 of the X-ray mirror 46. The width of the mirror 46 (i.e. the height in FIG. 2) is substantially greater than the length of line focus 41 as will be explained in more detail with reference to FIGS. 3a and 3b. The rays emanating from line focus 41 are indicated with reference numeral 42. Because the line focus 41 is arranged in the focal line of the surface 50, after reflection by the X-ray mirror 46 this beam is converted into a beam 52 the rays of which are practically mutually parallel in a plane perpendicular to the line focus 41. The (small) divergence of the reflected beam 52 is determined by the width of the focus line 41 as seen from the mirror 46. After leaving the X-ray mirror 46, the X-ray beam 52 strikes the monochromatizing element 48 which, in this Figure, is formed by a known two-crystal monochromator which consists of a pair of X-ray reflecting crystal surfaces 54 and 56. The pair of surfaces 54 and 56 is formed in a known manner by a U-shaped part which is cut from a germanium monocrystal. Reflection then takes place from the inner sides of the limbs of the U. The incident, practically non-diverging X-ray beam 52 (having a divergence of f.i. 0.025°) is monochromatized and further parallelized (having a divergence of f.i. 0.006°) by the reflection by the two-crystal surfaces, so that the X-ray beam 62 leaving the influencing device has been parallelized as well as monochromatized.

Figure 3A:
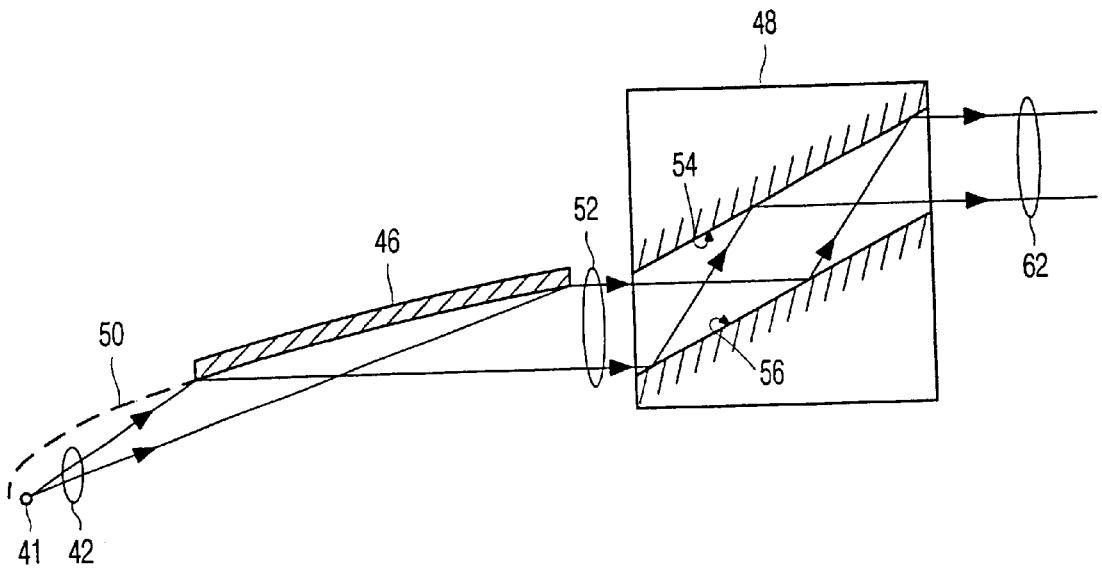
FIGS. 3a and 3b are a diagrammatic side elevation and plan view, respectively, of the X-ray mirror and the monochromatizing element, both forming part of the influencing device according to the invention, showing the dimensions and the relative positions of these elements appear.
Figure 3B:
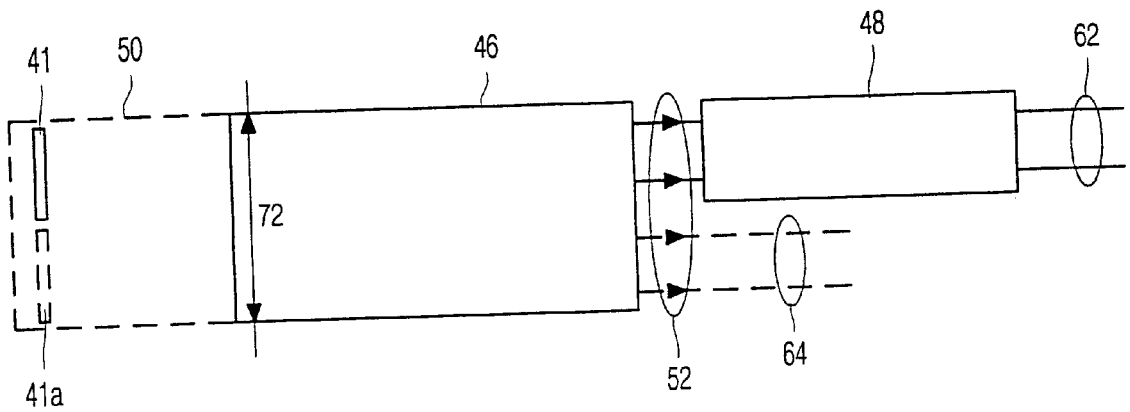

The FIGS. 3a and 3b diagrammatically show how parallelized or parallelized as well as monochromatized X-rays can be derived at option from the influencing device according to the invention. The Figures show the relative positions of the two X-ray optical elements used.

In the side elevation of FIG. 3a the parabolically curved surface of the X-ray mirror 46 extends perpendicularly to the plane of drawing, like the line focus 41. In the plan view of FIG. 3b the rectangle denoted by the reference numeral 46 constitutes the projection of the parabolically curved surface of the X-ray mirror 46 on the plane of drawing, so that in this rendition the line focus 41 lies in the plane of drawing. The length of the line focus 41 amounts to approximately half the width 72 of the X-ray mirror, see FIG. 3b. Subsequent to the X-ray mirror 46 there is arranged a monochromator 48 which is proportioned in such a manner that it receives only the radiation originating from a part of the X-ray mirror 46. This can be achieved by way of a suitable choice of the dimensions of the reflecting surfaces 54 and 56. When the combination consisting of the X-ray mirror 46 and the monochromator 48 occupies the position shown in FIG. 3b relative to the line focus 41, the radiation 52 originating from the X-ray mirror 46 passes through the monochromator 48. Said combination can be displaced in a direction parallel to the line direction of line focus 41, so that the combination occupies a position relative to the line focus which corresponds to the appearance 41a of the line focus which is denoted by a dashed line in FIG. 3b.

The X-ray beam 42 in the FIGS. 3a and 3b is produced by the line focus 41 or 41a. This beam is reflected by the parabolic surface 50 of the X-ray mirror 46 and leaves the mirror as a practically parallel beam 52. In the position 41 of the line focus the beam 52 traverses the monochromator 48 and leaves the monochromator as a beam 62. In the position 41a of the line focus the beam 52 bypasses the monochromator 48 and leaves the X-ray mirror 46 directly as the beam 64. Consequently, by displacing the combination 46, 48 parallel to the line direction of the line focus, a choice can be made between a first radiation channel which includes the X-ray mirror 46 and the monochromator 48 and a second radiation channel which includes only the X-ray mirror 46.

Figure 4:
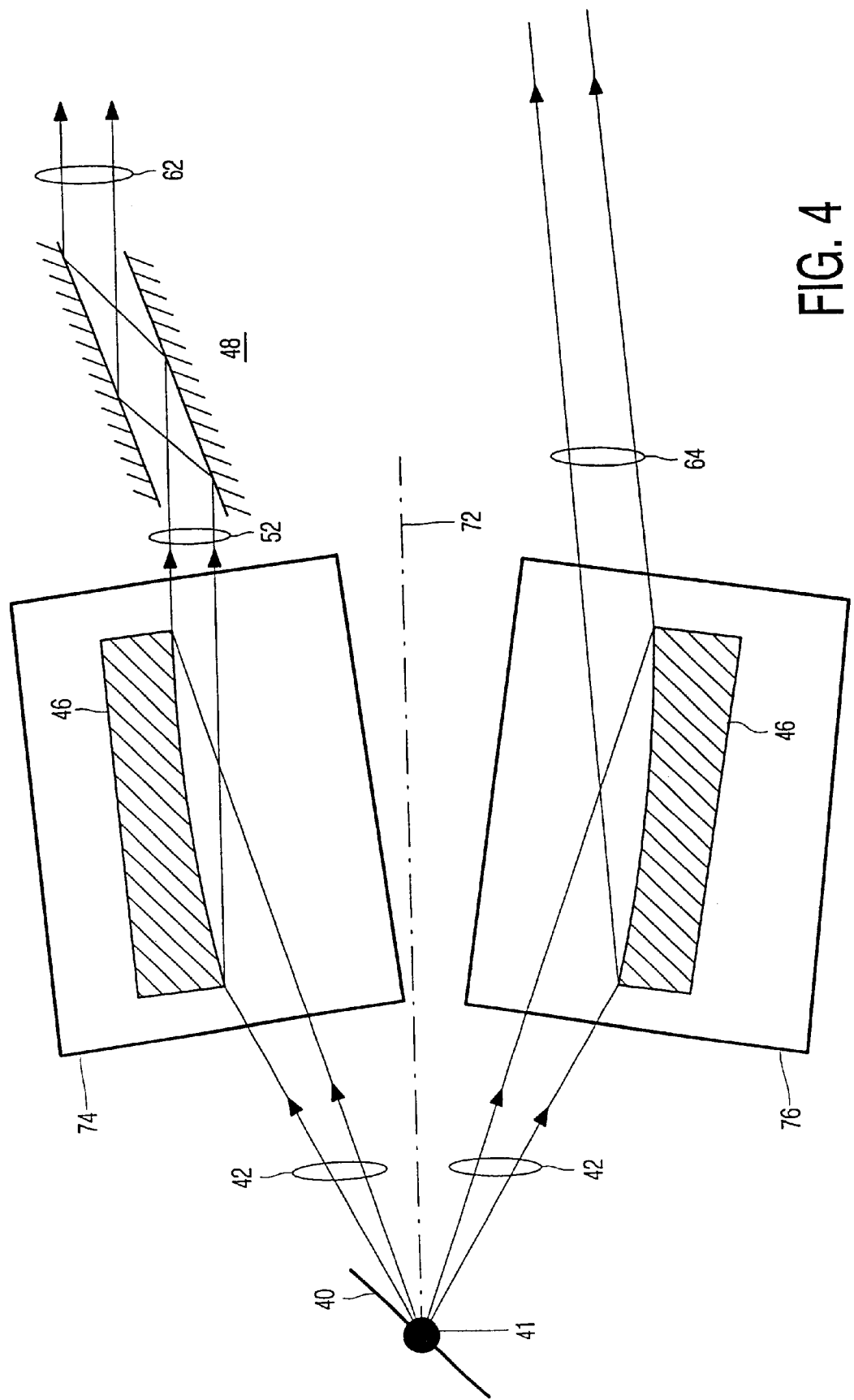
FIG. 4 is a diagrammatic representation of beam paths in a preferred embodiment of the influencing device according to the invention.

FIG. 4 is a diagrammatic representation of the beam path in a preferred embodiment of the influencing device according to the invention. This Figure shows the influencing device twice, in a first position 74 i.e. in the upper part of the Figure in which the X-ray beam travels via the X-ray mirror 46 as well as the monochromator 48, and in a second position 76 in the lower part of the Figure in which the X-ray beam travels only via the X-ray mirror 46. The influencing device changes over from the first to the second position and vice versa by rotation through an angle of 180° about an imaginary axis 72. The monochromator 48 is diagrammatically represented as a two-crystal monochromator in this Figure; in other words, this Figure shows only two reflecting surfaces. It is to be noted that in this embodiment of the invention the line focus 41 in the two positions is seen at a different angle from the X-ray mirror 46. In the second position 46, the anode 40, and hence the line focus 41, is seen at an angle of approximately 8° from the X-ray mirror, so that the divergence of the beam 64, determined by the observed width of the line focus, has a comparatively high value and a comparatively high X-ray intensity reaches the X-ray mirror. In the first position 74, the line focus 41 is seen at a smaller angle from the X-ray mirror, for example an angle of 4°, so that the divergence of the beam 52, determined by the width of the line focus observed in the relevant position, has a lower value. As has already been described, the latter situation may be necessary so as to achieve the small divergence required for the monochromator, for example in order to isolate one of two lines of an X-ray doublet (for example, the spectral lines $K_1$ and $K_2$ of a copper anode) by removing the other line from the beam spectrum.

Figure 5:
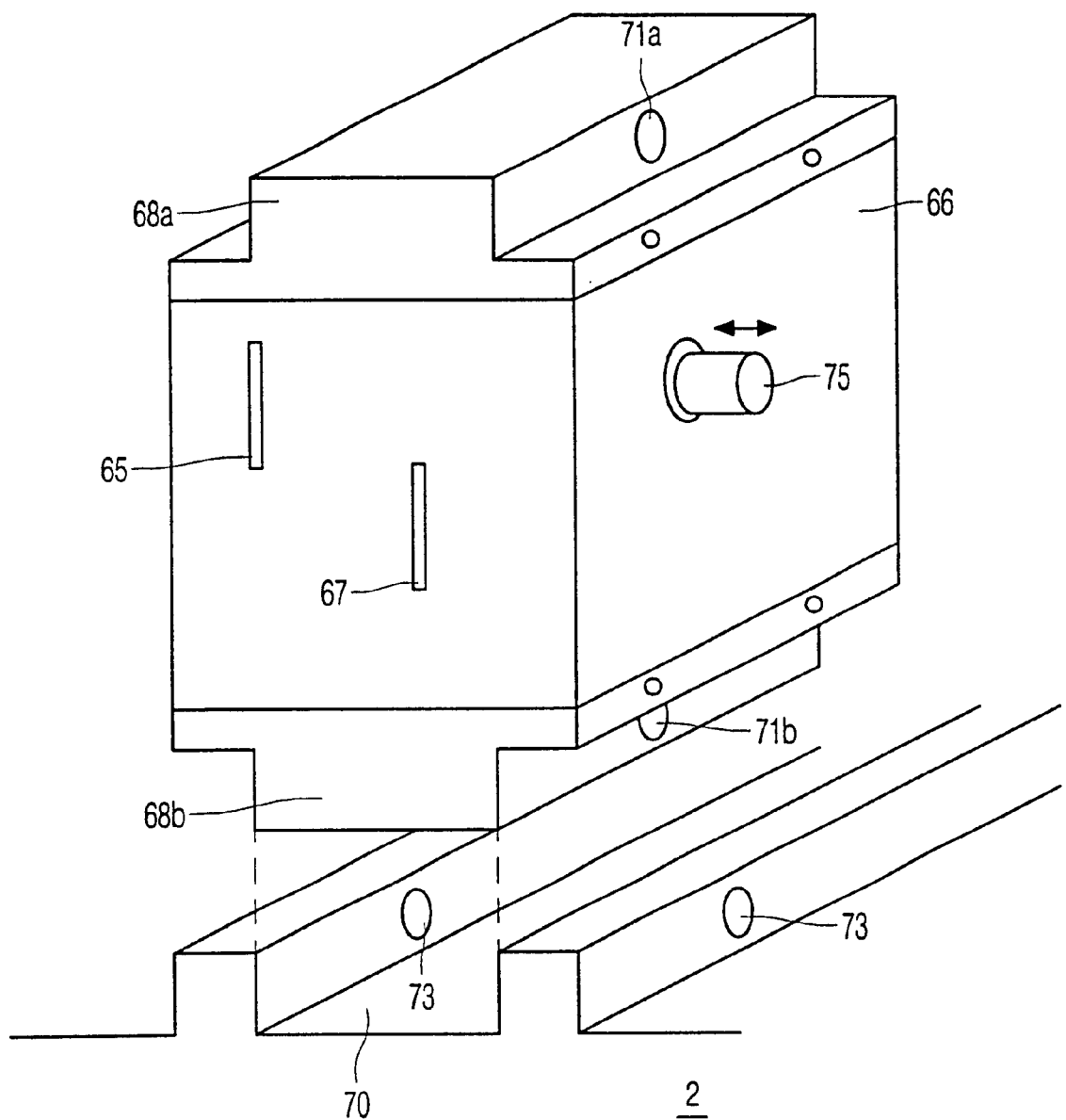
FIG. 5 shows an embodiment of the housing of the influencing device with positioning means according to the invention for positioning in the beam path between the X-ray source and the detector.

FIG. 5 shows an embodiment of the housing of the influencing device with positioning means according to the invention for the positioning in the beam path between the X-ray source and the detector. The Figure shows the housing 66 of the influencing device according to the invention which is provided with a entrance slits 65 and 67 for passing the X-ray beam through the first radiation channel and the second radiation channel, respectively, to be influenced to the influencing device accommodated in the housing 66. The first radiation channel of the influencing device contains the X-ray mirror 46 and the monochromatizing element 48 and the second radiation channel only contains the X-ray mirror 46. By means of a shutter device 75 (not shown) the first radiation channel can be closed and the second one be opened, and vice versa.

The housing 66 is provided with positioning means for positioning the housing in the beam path between the X-ray source 7 and the detector 30 as desired. The part of the positioning means provided on the housing 66 as shown in this Figure is formed as two T-shaped projections 68a and 68b which are situated on both sides of the housing 66 and each of which is intended to engage a corresponding U-shaped groove 70 provided in the frame 2 of the X-ray analysis apparatus. The projections 68a and 68b on the one side and the groove 70 on the other side thus constitute a system of co-operating positioning means. The housing 66 can be arranged in a first position in which the projection 68b engages the groove 70, and in a second position in which the projection 68a engages the groove 70. Each of the both projections 86a and 68b is provided with bores 71a and 71b respectively, the position of which during operation can be made coincident with bores 73 in the wall of groove 70, for exactly positioning the housing in de longitudinal direction of groove 70. When the X-ray mirror 46 and the monochromator 48 are suitably arranged in the housing, the change over from the position 74 to the position 76 and vice versa, as shown in FIG. 4, is realized by reversing the housing.

Evidently, it is possible to embody the co-operating positioning means in such a way that more than two positions are possible. Finally it is to be noted that the influencing device can be arranged not only in the beam path between the X-ray source and the sample to be examined, but also between the sample and the detector.

What is claimed is:

1. An X-ray analysis apparatus which includes:
   a sample location (8) for receiving a sample (10) to be examined,
   an X-ray source (7) for irradiating the sample (10) by means of X-rays,
   a detector (30) for detecting X-rays emanating from the sample (10),
   an influencing device (46, 48) which is constructed as a single mechanical unit (66), serves to influence the X-rays, and is arranged in a beam path (42, 45) between the X-ray source (7) and the detector (30),
      said device including two x-ray optical elements including a monochromatizing element (48) and an X-ray mirror (46) with a second-order reflecting surface (50), at least one of said two X-ray optical elements (46, 48) being situated in said beam path (42, 45),
   a frame (2) for positioning at least the influencing device in the beam path between the X-ray source and the detector, characterized in that
   the influencing device (46, 48) is constructed so as to include a first radiation channel (42, 52, 62) which comprises the X-ray mirror (46) and the monochromatizing element (48), and a second radiation channel (42, 52, 64) which comprises only the X-ray mirror (46),
   the influencing device, constructed as a single mechanical unit (66), and the frame (2) of the apparatus are both provided with co-operating positioning means (68a, 68b, 70) which are constructed in such a manner that the influencing device in the apparatus can occupy, at option, a first position (74) in which the first radiation channel (42, 52, 62) is positioned in said beam path, or a second position (76) in which the second radiation channel (42, 52, 64) is positioned in said beam path.

2. An apparatus as claimed in claim 1, in which the second-order reflecting surface (50) of the X-ray mirror (46) is a parabolic surface.

3. An apparatus as claimed in claim 2, in which the X-ray mirror (46) is a multilayer mirror.

4. An apparatus as claimed in claim 3, in which the multilayer mirror (46) is constructed as a multilayer mirror having a changing layer spacing.

5. An apparatus as claimed in claim 1, in which the monochromatizing element (48) is constructed as a crystal monochromator.

6. An apparatus as claimed in claim 5, in which the crystal monochromator (48) is provided with at least two reflecting crystal surfaces.

* * * * *